United States Patent [19]

White, Jr. et al.

[11] Patent Number: 4,914,966

[45] Date of Patent: Apr. 10, 1990

[54] AUTOMATED ULTRASONIC PROBE HOLDER FOR A SAMPLE FEEDER

[75] Inventors: Ralph T. White, Jr., Pfafftown; Dewey L. Holt, Winston-Salem; Jerry S. Simmons, Rural Hall, all of N.C.

[73] Assignee: R. J. Reynolds Tobacco Company, Winston-Salem, N.C.

[21] Appl. No.: 284,889

[22] Filed: Dec. 15, 1988

[51] Int. Cl.$^4$ ............................................ G01N 35/06
[52] U.S. Cl. .............................. 73/863.01; 73/864.85; 73/864.81; 356/36; 356/326
[58] Field of Search ........... 73/864.81, 864.82, 864.83, 73/864.84, 864.85, 864.86, 864.87, 863.01; 356/36, 326–330

[56] References Cited

U.S. PATENT DOCUMENTS 3,915,011 10/1975 Nelson ............................... 73/864.35
4,265,544 5/1981 Banno et al. ......................... 356/427
4,554,255 11/1985 Ishii et al. ..................... 73/863.02 X

FOREIGN PATENT DOCUMENTS 84544 4/1986 Japan .

OTHER PUBLICATIONS

"Sampling Method For Analysis of Solid-Liquid Slurry", *Patent Abstracts of Japan;* AB5 GRPNo: p. 493, Abs., vol. 10, No. 256, Abs. Pub. Date Sep. 2, 1986, Ogura et al [English Abstract of Japanese Pat. Document, No. 61–84544 (Refil)].

*Primary Examiner*—Tom Noland

[57] ABSTRACT

Apparatus for performing analysis of a slurry including solid particles of elements in a liquid suspension has a container for receiving a sample of the slurry to be analyzed, and a conveyor for moving the container to a location at which the analysis is to be performed. A sampling probe is to be introduced into the slurry sample to perform the analysis. A separate probe is adapted to ultrasonically agitate the slurry sample to keep the solid particles in suspension. The agitating probe is automatically introduced into and withdrawn from the container in synchronism with the movement of the container into the desired location and immediately prior to the introduction of the sampling probe into the slurry sample.

15 Claims, 3 Drawing Sheets

AUTOMATED ULTRASONIC PROBE HOLDER FOR A SAMPLE FEEDER

FIELD OF THE INVENTION

The present invention relates to sampling systems for atomic absorption spectrometers utilized to analyze slurry samples, and more particularly to an improved apparatus in which the holder for an ultrasonic probe is automated to provide mixing of finely ground particles to produce a suspended, well-mixed slurry immediately before the sampling and subsequent analysis steps.

BACKGROUND OF THE INVENTION

Atomic spectroscopy is a technique useful for analyzing the constituent elements of a sample of material of interest. By way of example, the sample may be processed in an ultrasonic processor for the determination of metallic and semimetallic elements in the sample, using flame atomic absorption or graphite furnace atomic absorption. A typical sample to be subjected to such elemental analysis consists of a slurry of insoluble matter in a liquid suspension, such as solid particles suspended in solution.

Of particular interest is the elemental analysis of slurries in which solid particles of 325 mesh (44 microns) sieve designation or smaller, and more particularly in the range from 50 to 170 mesh (297 to 88 microns) sieve designation, are suspended in water or an organic liquid such as methanol. A consistent slurry, in terms of regular particulate size and concentration in the solution, tends to produce a more precise and accurate analysis than would otherwise be achieved. Yet, it is difficult to obtain the desired precision and accuracy in the elemental analysis of a slurry. This is because the slurry is formed by mixing its constituents together, after which a portion of the slurry is taken as a sample and transferred to a sample cup for purposes of performing the analysis. With the passage of even a brief period of time from the mixing to the transfer and commencement of analysis, the solid particles have begun to precipitate or settle out of the suspension. As a consequence, the true elemental content of the slurry may escape analysis. It is imperative that the sample be kept in uniform suspension to assure accurate analysis and determination of the elements of interest.

As a result, it would be desirable to provide a method and apparatus for improving the accuracy and precision of spectroscopic analysis of a slurry sample by maintaining the solid particles of the sample in suspension by agitation thereof until virtually the last instant prior to performing the analysis.

Prior art techniques for agitating liquid samples prior to analysis generally involve the use of special means for shaking the apparatus and holding the sample, such as a vibrating table or receptacle. A representative example of such prior art techniques is described in U.S. Pat. No. 4,265,544 to Banno et al (hereinafter referred to as the "Banno technique"). The Banno technique is intended for automatic agitation of a reaction solution consisting of a mixture of a liquid to be examined and a reagent. In its implementation, mechanical vibration is imparted to apparatus holding the sample by a rotary solenoid energized for a preselected time interval by an oscillator. During that interval, the sample holder undergoes reciprocating movement.

Such a technique requires that the entire apparatus cease moving before the analysis can be performed, or that the sample be transferred to another location for analysis. Because the sample undergoing analysis in the Banno technique is not a slurry, but a solution composed entirely of a liquid and a reagent, the effect of a delay between agitation and analysis may be minor in that circumstance. That is, the settling down of the apparatus is not likely to be accompanied by a settling out of the particulate matter from solution. Rather, the Banno technique addresses the problem of agitating the solution in a manner that will keep its constituents thoroughly mixed while avoiding a change of the temperature of the sample which might affect the analysis.

Prior art techniques for agitating a liquid sample under analysis typically present the further difficulty of requiring the movement of a large mass, such as the reciprocation of a holding table, in order to achieve the desired agitation. In such arrangements, it is often necessary to provide complex and bulky apparatus to produce the movement of the larger mass, and thereafter dampen the movement to return the mass to a steady state within a reasonably brief period of time, so that the analysis may be commenced while the solution is still thoroughly mixed.

It has been proposed in the prior art to agitate a sample under analysis by manually inserting an ultrasonic probe into the sample cup, and thereby keep the solid particles in suspension prior to performing the analysis. This technique, however, interferes with the smooth continuous operation of the atomic spectroscopy apparatus, as it requires that the apparatus be stopped during the agitation step. Moreover, the manual step must be performed with great care to avoid disturbing any portion of the apparatus or of the sample cups themselves. Also, manual activation and deactivation of the probe, coupled with the need to restart the equipment thereafter, allows at least partial resettlement of particles from the suspension, thereby making the results of the analysis less accurate.

It is another object of the present invention to provide methods and apparatus for agitating a slurry under analysis in a manner which allows the analysis to be performed virtually instantaneously after the agitation has ceased, without the need to wait for the apparatus to settle down.

Yet another object of the present invention is to provide a technique for maintaining solid particles in liquid suspension in a slurry sample under spectroscopic analysis to determine the elemental content thereof, by means which avoid the need for movement of massive parts of an apparatus.

It is yet another object of the present invention to provide an improved technique for maintaining the solid particles of a slurry sample under analysis suspended in solution automatically, that is, by a self-acting mechanism that repeatedly agitates the slurry, without interfering with the apparatus performing the analysis.

SUMMARY OF THE INVENTION

According to the present invention, an ultrasonic probe is adapted to be operated automatically for selfactuated movement from a normal rest position to a position in direct contact with a sample of a slurry under analysis in a sample holder, at a predetermined point in the process of analyzing the sample. During this automatic operation, when the probe is in contact with the slurry sample it is energized to ultrasonically agitate the slurry to maintain the solid particles therein in suspension within the solution. As a further part of the automatic operation, the ultrasonic probe is deenergized, withdrawn from the slurry sample to be analyzed, and returned to the rest position immediately prior to the introduction of a distinct and different sampling probe into the sample in conjunction with the analysis.

As used in this patent specification, the terms "immediately" and "instantaneously," when used in connection with the interval between ultrasonic agitation of the slurry sample and entry of the sampling probe for purposes of the analysis, mean an interval of time less than that during which the suspended particles will appreciably settle out of the solution. As a practical matter, the interval is less than 10 seconds, and in the preferred embodiment of the invention is in the range from 0.01 to two seconds.

According to a feature of the invention, the apparatus is arranged and adapted to avoid interference between the movement of the ultrasonic probe and the movement of the sampling probe when the former is withdrawn from and the latter is being introduced into the sample mixture, or interference between the ultrasonic probe and any other part of the apparatus.

In a preferred embodiment of the invention, the ultrasonic probe is held in a rest position relative to the location into which the slurry sample reservoir (i.e., cup) is to be moved for analysis. A sensor detects the entry of the sample cup into the proper position, to activate the probe holder and thereby move the ultrasonic probe downwardly into the cup by means of a pneumatically actuated piston. Simultaneously therewith, the probe is energized to cause the ultrasonic agitation of the slurry sample. Sensors associated with the activation apparatus for the ultrasonic probe holder reverse the piston movement at a time just prior to the introduction of a sampling probe into the cup. The sampling probe then extracts a specimen of the slurry sample from the cup for purposes of atomic spectroscopic analysis. Hence, the ultrasonic probe is withdrawn from the cup before the sampling probe is moved into position in the cup, thereby avoiding interference between the two probes.

BRIEF DESCRIPTION OF THE DRAWINGS

The above and still further objects, features, and attendant advantages of the present invention will become apparent from a consideration of the following detailed description of a preferred embodiment thereof, taken in conjunction with the accompanying drawing in which.

DESCRIPTION OF THE PREFERRED EMBODIMENT

The presently preferred embodiment of the invention will be described in the environment of apparatus for performing flame atomic absorption spectroscopy, such as conventional apparatus of the type produced, for example, by the Perkin-Elmer Company. Exemplary apparatus of this type includes the Perkin-Elmer Model 5000 Atomic Absorption Spectrometer, equipped with an HGA-500 graphite furnace and AS-40 graphite furnace auto sampler; and the Perkin-Elmer Model Zeeman/3030 Atomic Absorption Spectrometer equipped with HGA-600 graphite furnace and AS-60/70 graphite furnace autosampler. It should be emphasized, however, that according to an important feature, the present invention may be incorporated during manufacture into such sample analyzing apparatus, or it may be produced as a stand-alone unit for subsequent use in conjunction with existing conventional sample analyzing apparatus.

Figure 1:
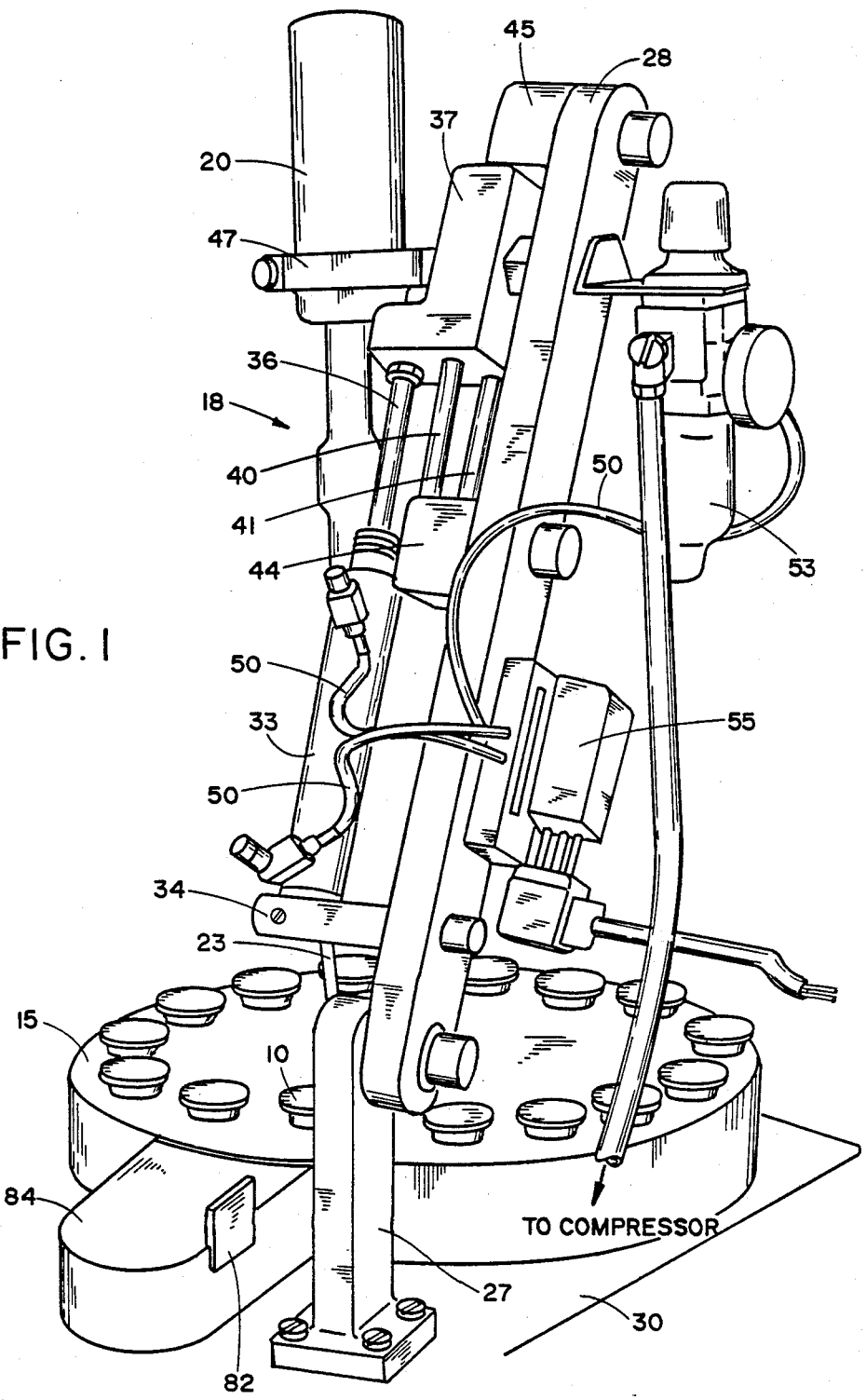
FIG. 1 is a perspective elevational view of the apparatus of the preferred embodiment of the invention, taken in one direction.
Figure 2:
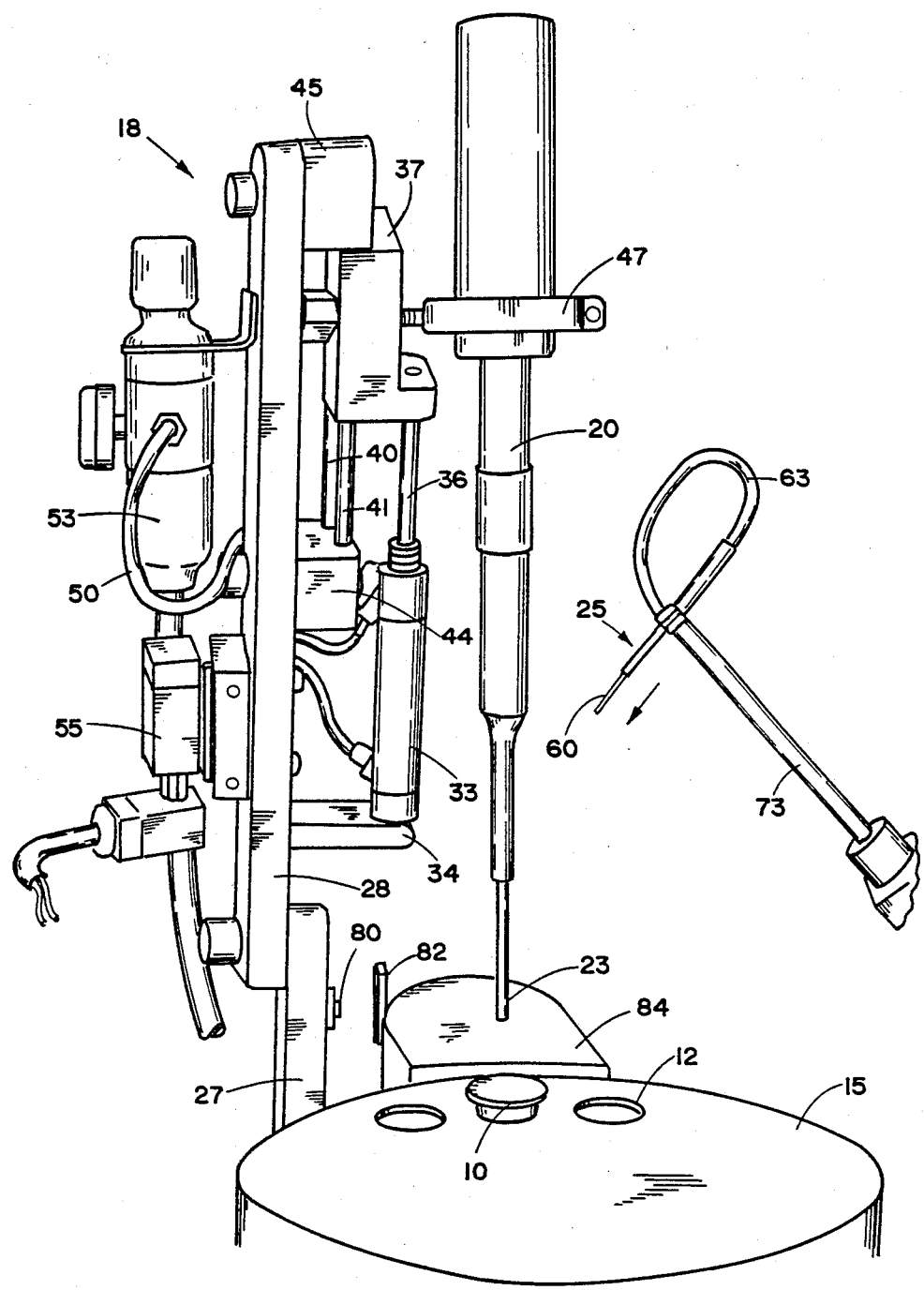
FIG. 2 is a perspective elevational view of the apparatus of the preferred embodiment, taken in the direction opposite that of FIG. 1.

Referring now to FIGS. 1 and 2, a Perkin-Elmer spectrometer such as one of those described above has a rotary conveyor or feeder 15 mounted for selective clockwise and counterclockwise movement in the horizontal plane. The feeder 15 has a plurality of receptacles 12 adapted to receive and retain reservoirs or cups 10, which may contain samples of the same slurry or different slurries each consisting of a mixture of solid particles suspended in solution in a liquid such as water or methanol. By way of example, the particles in a slurry sample typically are of sizes down to 325 mesh (44 microns) or smaller sieve designation. In the analytical apparatus with which the preferred embodiment of the present invention is employed, the desired range of the solid particles is from 50 to 170 mesh (297 to 88 microns) sieve designation, and their concentration in the liquid carrier ranges from 0.01 to 1.4 micrograms per milliliter. For the sake of illustration, one or more of the slurry samples under analysis may be an aqueous mixture of tobacco parts which is to be analyzed to ascertain the trace elemental content, if any, of certain metals or semimetals.

The sample feeder 15 may be operated selectively to undergo indexed rotation, to move a sample cup 10 to a desired location for analyzing the sample or a specimen thereof. An alternative form of conveyor may, for example, be a surface feeder adapted for X-Y movement in the horizontal plane. In any event, such conveyors typically are part of the conventional spectrometer apparatus, such as the Perkin-Elmer models mentioned above.

Figure 3:
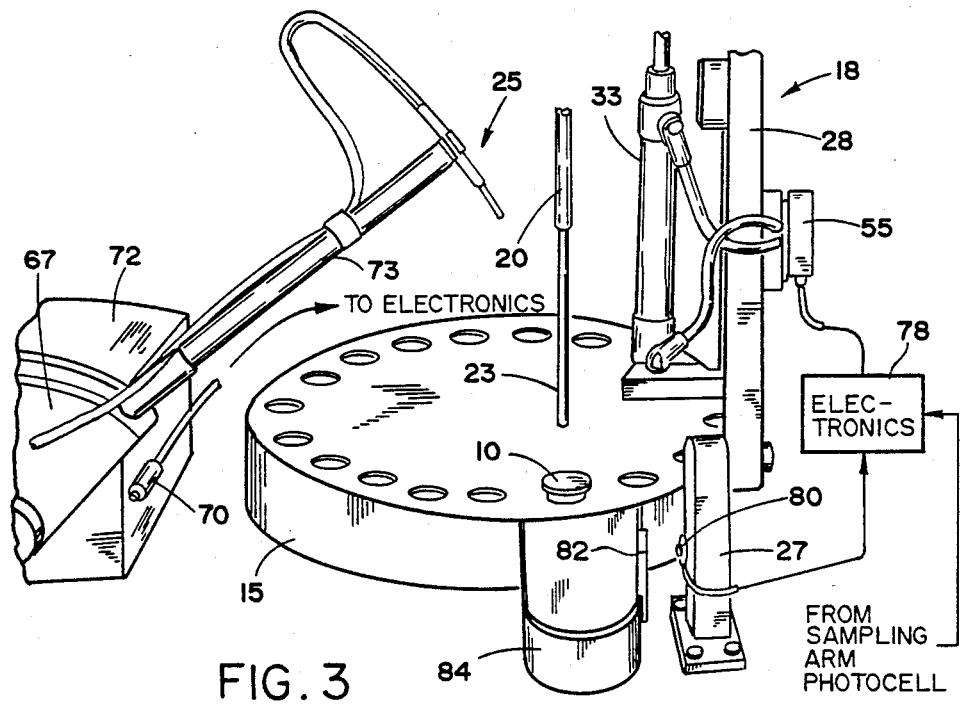
FIG. 3 is a detailed perspective view of a portion of the apparatus of FIGS. 1 and 2, to more clearly show the elements utilized to avoid interference between the two probes during movements thereof.

According to the invention, an automated holder 18 for an ultrasonic probe 20 may be manufactured as a part of such conventional spectrometer analysis, or may be fabricated separately as a stand-alone subsystem which can be utilized in practice together with such apparatus. The principal purpose of automated holder 18 is to retain, suspend, and automatically raise, lower, swivel, and energize ultrasonic probe 20. As shown in FIGS. 1, 2 and 3, the tip 23 of the probe 20 is normally disposed in its rest position at a point above and offset from a cup 10 which has been moved by sample feeder 15 into the desired location for analysis of the contents of the cup. That location of a sample cup is hereinafter referred to as the location for analysis.

Accordingly, during that interval, the probe tip is held out of contact with the surface of the material contained in the cup, but it is poised for introduction into (or merely to touch) the material at an appropriate time in the analytical process, in a manner to be described in detail presently. Upon introduction of tip 23, the probe is energized for a predetermined time interval for ultrasonic agitation of the contents of the cup. In the example where the cup contains a slurry of a type described above, the ultrasonic agitation serves to maintain the solid particles in suspension in the liquid. A typical analytical cycle for the slurry in the aforementioned Perkin-Elmer apparatus takes on the order of two minutes, and the agitation is set to occupy an interval of, say, ten to fifteen seconds just before the actual analysis is commenced. After the predetermined period of agitation of the slurry, ultrasonic probe 20 is retracted by holder 18 to withdraw tip 23 from the cup 10 positioned in the location for analysis.

An important feature of the invention is that the operation of ultrasonic probe 20 is synchronized with the operation of a sampling probe 25 (FIGS. 2 and 3), the latter being part of the conventional analytical process. As with the ultrasonic probe, the sampling probe is arranged and adapted for movement to periodically introduce its tip into and out of cup 10. The purpose of the sampling probe, however, is to withdraw a specimen of the material to be analyzed from the cup. The spectroscopic analysis itself is entirely conventional and need not be further elaborated on for purposes of understanding of the present invention. The reader is referred to descriptive literature available from the particular spectrometer manufacturer, such as Perkin-Elmer, if further details of the structure or operation of that equipment are desired.

In the presently preferred embodiment of the invention, ultrasonic probe holder 18 includes a pair of beams 27 and 28. The lower beam 27 is fastened and extends upright relative to the surface 30 on which the rotary feeder 15 is disposed, and the upper beam 28 is inclined at an angle to the lower beam. The angle of inclination is adjustable by means of an appropriate fastener, such as a thumbscrew 29, and its particular value is not critical. In the preferred embodiment, for example, this angle is approximately 45 degrees. The significant aspect is that there be flexibility, through adjustment of the angle of inclination, to maneuver the probe for proper positioning relative to the cup in the location for analysis. In this way, the probe is arranged so that upon activation in a manner described below, tip 23 is thrust from its rest position into a contact position with the slurry sample in the cup, and, upon completion of the period of ultrasonic energization, is withdrawn or retracted to the rest position once again.

Sample feeder 15 is selectively rotatable clockwise or counterclockwise to place a cup 10 in the location for analysis. After the sample therein has been subjected to analysis, the conveyor is shifted in the sequencing process to bring the next sample cup 10 into that location, in which tip 23 of ultrasonic probe 20 may again be activated from the rest position to the contact position.

A pneumatically-actuated piston 33 is connected to an arm 34 extending from beam 28 and, at the shaft 36 of the piston, to a separate slidable member 37. When the shaft 36 is extended or withdrawn, member 37 slidably moves along rods 40 and 41 extending therethrough between spaced blocks 44 and 45 fastened to the upper beam 28 of holder 18. A clamping ring 47 is affixed to slidable member 37 to lock the ultrasonic probe 20 to that member. The piston 33 is actuated by pressure exerted from the air delivered via tubing 50 from a chamber 53 (FIG. 2) coupled to a compressor (not shown), under the control of a solenoidal power valve 55. When valve 55 is operated such that pressure is delivered to piston 33, the piston shaft 36 moves outward until fully extended, whereupon slidable member 37 is forced up against the stop provided by upper block 45. In that configuration, ultrasonic probe 20 is in the rest position shown in FIG. 2, with its tip 23 lying above and offset from the surface of the slurry in the sample cup 10 in the location for analysis.

The air actuated piston/cylinder for the ultrasonic probe is commercially available, and the air pressure is controlled by the solenoid valve 55 such that energizing the solenoid valve coil causes the ultrasonic probe to move down to its contact position. De-energizing the solenoid valve allows the air pressure to return the probe to its rest position. This type of operation assures that the ultrasonic probe "defaults" (that is, is returned) to the rest position in the event of a power failure.

When valve 55 is actuated to exhaust air from piston 33, shaft 36 is withdrawn into the piston body. Slidable member 37 and clamping ring 47 secured thereto are thereby lowered along rods 40 and 41 until member 37 bottoms against the stop provided by lower block 44. As air is withdrawn from the piston into chamber 53, ultrasonic probe 20 is lowered in its vertical orientation relative to the surface of conveyor 15, but along the angle of inclination determined by the adjustment of the orientation of upper beam 28 relative to lower beam 27. The relative positioning of the various members of the holder apparatus is such that the probe tip 23 is introduced into the cup 10 in location for analysis, and finally into contact with the slurry sample therein, by the time member 37 bottoms against the stop 44.

As that point in the operation of the automated holder, an electromechanical converter in the probe 20 is then energized by a power supply (not shown) to produce ultrasonic vibration of tip 23, from which the vibrations are transmitted to agitate the slurry sample in cup 10 at ultrasonic frequencies. As a consequence of this agitation, the solid particles are maintained in suspension in the liquid of the slurry. The period of agitation is preferably in the range from 10 to 15 seconds, depending on the type of slurry under analysis; however, the period will also depend in some part on the time interval required for analysis of the sample. As previously observed, in equipment of the Perkin-Elmer type for spectroscopic analysis of interest in the preferred embodiment of the invention, the analytical cycle is approximately two minutes in length. The frequency of the agitation may be any within the normal ultrasonic range, inasmuch as frequencies in this range will tend to assure greater uniformity of concentration of the particles throughout the liquid carrier.

Suitable embodiments of the ultrasonic probe (converter, horn, coupler and tip) and the ultrasonic power supply and connections therefor are standard products available from the Tekmar Company of Cincinnati, Ohio. The tip of the ultrasonic probe should be composed of a material which will not contaminate the slurry sample to be analyzed, or affect the results of the analysis depending on the types of trace elements sought to be detected. For example, one should not use a stainless steel probe tip where the analysis is for trace amounts of nickel, chromium and/or iron. Titanium is preferred for the probe tip material in the case of analysis of an aqueous slurry of tobacco parts of the type mentioned above, although other materials are suitable as well. The important consideration is that contamination should be avoided for the sake of accurate analysis.

Another consideration in avoidance of contamination is the prevention of sample-to-sample contamination. To that end, it is recommended that following each analysis the probe tip should be immersed in water or alcohol, or other liquid corresponding to that of the slurry under analysis, and that the ultrasonic power supply should be energized for a few seconds to remove any residue from the tip. By way of example, the sample cups may be arranged in a sequence so that cups holding samples to be analyzed are alternated with cups holding cleansing liquid. However, in the presently preferred embodiment, no significant sample-to-sample contamination has been detected even when cleaning of the ultrasonic probe tip between samples is omitted. The function of cleaning the ultrasonic probe tip is achieved using a wash station in a manner which will be described presently.

Still another consideration in avoiding contamination, as well as preventing interference between moving parts of the apparatus, is the movement and final positioning of the probe prior to ultrasonic agitation of the sample. It is highly preferred that the probe should be positioned such that when the tip is introduced into the cup there is contact with nothing but the sample to be analyzed. The contact need not extend beyond the surface of the sample; however, contact with any part of the cup itself, especially when the ultrasonic vibration is taking place, can cause disruption of the cup surface and allow tiny particles therefrom to migrate into the sample. It will be apparent that this could affect the results of the analysis, and, therefore, should be avoided.

To obtain a specimen from the sample under analysis, it is necessary (and conventional) to introduce a sampling probe 25 (FIGS. 2 and 3) into the sample cup 10 for withdrawal of a suitable specimen quantity of the sample which is to undergo the atomic absorption spectroscopy. For withdrawal of the specimen, the sampling probe includes a hollow-tipped Teflon ® needle 60. The specimen (5 to 100 microliters) is withdrawn into the sampling probe by an automatic syringe connected with tubing 63 to the needle and then deposited into the spectroscopic analyzer. Typically, the sampling probe 25 is arranged within a holder 67 to pivot in an arc through an angle of approximately 45 degrees into and out of the sample cup, as is shown most clearly in FIGS. 3 and 4.

Physical interference between the ultrasonic probe 20 and the sampling probe 25 should be avoided as they alternate in their travel into and from the sample cup. The alternation in movement takes place as follows. The sample cup is moved into position for analysis by the feeder 15, beneath and offset somewhat from the axis of the ultrasonic probe in the latter's rest position. The probe tip 23 is moved to its contact position with the surface of the slurry sample in the cup by the actuation of the piston 33. The probe 20 is then energized by the power supply to ultrasonically agitate the sample for about 10–15 seconds, and the tip 23 is then retracted to its rest position by the further actuation of the piston. Instantaneously thereafter (in a period of from 0.01 to 2 seconds in the preferred embodiment), the sampling probe is lowered from its rest position (as shown in FIGS. 2 and 3) into the cup to withdraw a specimen (5 to 100 microliters), and is then retracted from this specimen withdrawal position to its rest position. Movement of the sampling probe is effected by the operation of the conventional Perkin-Elmer apparatus.

Figure 4:
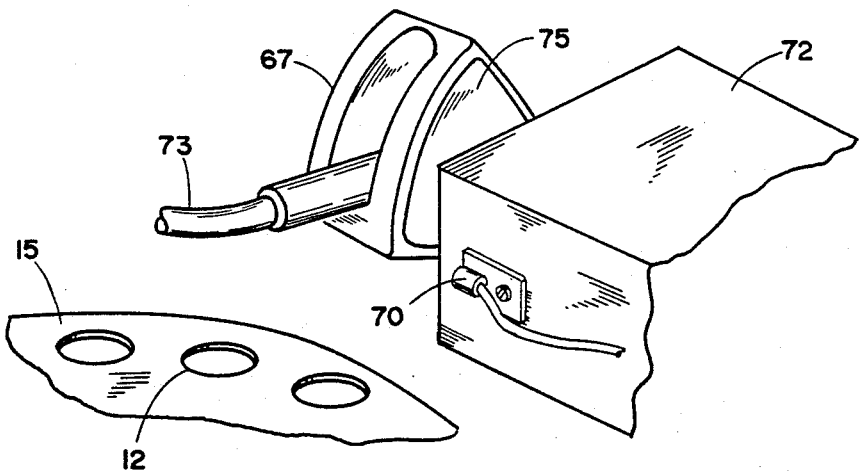
FIG. 4 is a further detailed perspective view of a portion of the apparatus, taken in a different direction from that of FIG. 3.

According to a feature of the invention, interference between the ultrasonic and sampling probes is prevented by use of a photoelectric system to monitor the location of sampling probe 25, i.e., to determine whether it is at its rest position or its specimen withdrawal position, and to monitor the position of the conveyor 15 to determine when a new sample cup is in the location for analysis of the sample therein. A first photocell 70, such as a Banner SP1OOD diffuse sensor, is mounted on the autosampler 72 of the spectrometer, on which the sampling probe 25 is pivotally mounted (FIGS. 3 and 4). Light is emitted from a point on photocell 70, but is not detected by the associated sensor when the sampling probe arm 73 is in its upper position. When the sampling probe arm is pivoted toward and into its specimen withdrawal position (and ultimately, back to its rest position), however, a reflecting surface 75 on the side of the pivotal bracket 67 holding the arm 73 causes the emitted light to be reflected back onto the sensor of the photocell 70.

During the time that the sensor is detecting the reflected light, the solenoid valve 55 is maintained, by conventional electronics 78 responsive to the electrical signal thereby generated by the sensor, in the condition in which air is supplied to the piston 33 (FIG. 3). In other words, the pneumatic system is inhibited from moving the ultrasonic probe 20 toward the sample cup. Hence, the tip 23 of the ultrasonic probe is held in its rest position above the sample cup, which is a position of non-interference with the movement of the sample probe.

A second photocell 80 (FIGS. 2 and 3), which may also be a Banner SP1OOD diffuse sensor, is mounted on the lower beam 27 of the ultrasonic probe holder 18 to emit and detect reflected light relative to a reflector 82 mounted on the side of a conventional plastic wash station 84 associated with conveyor 15 for the sample cups in the conventional spectrometer equipment. The wash station 84, which is connected to and part of the conveyor, moves toward and away from the location for analysis as part of the operation of the conventional apparatus. It moves away from the cup after the latter has reached that location. It moves toward the location and remains there after the analysis has been completed by the spectrometer, to allow the sampling probe to enter and be washed to remove any remaining slurry and residue. In essence, the liquid in the wash station is used to flush the inside and outside of the sampling probe tubing.

The reflector 82 is arranged such that when the wash station 84 is away from the cup, the reflector reflects the emitted light back toward the sensor of photocell 80. The electrical signal thereby generated by the photocell is utilized to actuate solenoid valve 55, by means of conventional electronics 78, to exhaust the air from piston 33. Accordingly, the tip of the ultrasonic probe is lowered to its contact position relative to the slurry sample in the cup. At that point, the ultrasonic power supply is activated by a timer within electronics 78 to cause the tip to agitate the slurry for the preselected time interval.

Electronics 78 (FIG. 3) includes the timer, logic circuitry to activate the timer when both sensors are active, and switching means to activate the power supply for the ultrasonic probe when it is in the contact position. An important feature of the present invention is that the automated holder is readily attached to existing conventional analytical equipment and cooperates with its functions without any modification to the hardware or programming of the existing equipment. The photoelectric sensors serve to monitor the usual motions of members of the conventional equipment and to lower and raise the ultrasonic probe independently at the appropriate times. The interval timed by the timer is preselected, based on the observed normal operation of the analytical equipment, to lower the ultrasonic probe from the rest position to the contact position upon passage of the preselected time interval, after the photosensor detects the raising of the sampling probe by the autosampler of the analytical equipment. The ultrasonic probe then remains in the contact position until the sampling probe commences its downward motion. This assures the synchronization of the movements of the two probes to avoid any interference therebetween. However, the energization of the ultrasonic probe tip is set preferably at the aforementioned 10-15 second interval, and the ultrasonic probe is retracted within the interval of 0.01 to 2 seconds before the sampling is effected.

In practice, the first sample cup 10 is filled with water or organic liquid (a "flush" sample, which may depend on the nature of the subsequent slurry samples to be analyzed) for the sake of activating the apparatus initially through one cycle of the movements of the various members as has been described. Each of the sample cups normally holds approximately 1.5 milliliters, but larger cups holding up to about 5 milliliters may be substituted, if desired. In operation of the apparatus, the graphite furnace and autosampler of the conventional spectrometer are programmed in the usual manner. The slurry to be analyzed is magnetically mixed using a stirring bar, and transferred to the sample cup(s). The automated ultrasonic probe holder is then activated by switching on and setting the timer in the electronics, and switching on the electronics for the ultrasonic probe. The spectrometer analysis programs are activated, and the sampling probes, and the other members of the apparatus and of the automated probe holder then proceed through the operations described above for each cycle (i.e., for each sample to be analyzed).

Although a presently preferred embodiment of the invention has been described herein, it will be apparent to those of ordinary skill in the art to which the invention pertains that variations and modifications of the described embodiments and processes may be made without departing from the spirit and scope of the invention. Accordingly, it is intended that the invention be limited only to the extent required by the appended claims and applicable rules of law.

What is claimed is:

1. Apparatus for analyzing the elemental content of a slurry having solid particles containing elements to be analyzed suspended in a liquid carrier, the apparatus comprising
   (i) cup means for receiving a sample of the slurry to be analyzed,
   (ii) positioning means for moving the cup means to a location for analysis,
   (iii) a first sample analysis probe means for withdrawing a portion of the sample from the cup means when in said location, for analysis thereof,
   (iv) a second sample agitation probe means for agitating the sample, and
   (v) means for (a) automatically introducing the second probe means into the cup means when in said location, to maintain the solid particles in suspension therein, and (b) removing the second probe means from the cup means substantially immediately prior to the withdrawal of said sample portion by the first probe means.

2. The apparatus of claim 1, further including means for energizing the second probe means to agitate the sample ultrasonically.

3. The apparatus of claim 1, the second probe means including a probe for contacting the sample, said probe comprising a material which is substantially noncontaminating relative to the slurry under analysis.

4. The apparatus of claim 3, wherein said material is titanium.

5. The apparatus of claim 1, the second probe means including a probe for contacting the sample, said probe comprising a material which is substantially non-contaminating relative to the elements to be analyzed in the slurry.

6. The apparatus of claim 1, further including means for synchronizing the movements of said first and second probe means to prevent interference therebetween.

7. The apparatus of claim 6, the synchronizing means including sensor means for detecting the movements of said first and second probe means.

8. A system for analyzing a slurry of solid particulate material suspended in fluid within a container movable to a location for sampling the slurry for the analysis, the system comprising automated means for maintaining the solid particulate material in suspension in the fluid to enable analysis thereof, the system further including
   (i) means for agitating the slurry ultrasonically,
   (ii) means responsive to movement of the container to said location for activating the agitation means, and
   (iii) means for withdrawing the agitation means from the slurry after a preset time interval ending prior to the sampling of the slurry for analysis.

9. The invention of claim 8, the activating means including means for synchronizing the agitation and the sampling to avoid interference of one with the other.

10. The invention of claim 9, the synchronizing means including means for detecting a first activity of one of agitation or sampling to initiate activity of the other of agitation or sampling as soon as the first activity ends.

11. A stand-alone system for use with a spectrometer for analyzing the content of elements in solid particles suspended in a liquid, the spectrometer having a conveyor for placing samples of the liquid bearing the solid particles into a predetermined location for analysis and having a sampling probe for withdrawing a portion of a sample for analysis by the spectrometer, the system comprising (a) an ultrasonic stirrer, and (b) means responsive to a sample in said predetermined location (i) for agitating the sample with the ultrasonic stirrer until the analysis is performed, and (ii) for keeping the solid particles in suspension in the liquid up to the time the sampling probe withdraws the sample portion.

12. The invention of claim 11, further including means associated with the agitating means for removing the stirrer from the sample under analysis to avoid interference with the sampling probe at the time the portion of the sample is to be withdrawn.

13. A process for analyzing the elemental content of a slurry having solid particles containing the elements to be analyzed suspended in a liquid carrier, the process comprising the steps of:
   (i) moving a container holding a sample of the slurry to a location for the analysis,
   (ii) introducing a first probe into the sample when the sample is in said location to agitate the sample, (iii) introducing a second probe into the sample to withdraw a portion thereof for analysis when the sample is in said location, and (iv) synchronizing the introduction and removal of the two probes relative to the sample to maintain the solid particles in suspension therein up to the withdrawal of the sample portion for the analysis without interference between the two probes.

14. The process of claim 13, the step of introducing the first probe into the sample including energizing the first probe ultrasonically.

15. The process of claim 14, the step of synchronizing including the step of sensing the movements of the first and second probes.

* * * * *